(12) United States Patent
Fertig et al.

(10) Patent No.: US 7,173,060 B2
(45) Date of Patent: Feb. 6, 2007

(54) OXIME DERIVATIVES AND THEIR USE AS PHARMACEUTICALLY ACTIVE AGENTS

(75) Inventors: Georg Fertig, Penzberg (DE); Frank Herting, Penzberg (DE); Manfred Kubbies, Penzberg (DE); Anja Limberg, Munich (DE); Ulrike Reiff, Penzberg (DE); Michael Weidner, Penzberg (DE)

(73) Assignee: Hoffmann-La Roche Inc.

( * ) Notice: Subject to any disclaimer, the term of this patent is extended or adjusted under 35 U.S.C. 154(b) by 489 days.

(21) Appl. No.: 10/814,410

(22) Filed: Mar. 31, 2004

(65) Prior Publication Data

US 2004/0214880 A1    Oct. 28, 2004

(30) Foreign Application Priority Data

Apr. 4, 2003    (EP) .................................. 03007829

(51) Int. Cl.
*A61K 31/381* (2006.01)
*C07D 333/10* (2006.01)

(52) U.S. Cl. .................. 514/448; 549/29; 549/70; 549/72; 546/268.1; 546/280.4; 514/4.38

(58) Field of Classification Search .................. 549/29, 549/70, 72; 546/268.1, 280.4
See application file for complete search history.

(56) References Cited

U.S. PATENT DOCUMENTS

| 3,810,910 A | 5/1974 | Meyer et al. |
| 5,137,918 A | 8/1992 | Weiershausen et al. |
| 6,784,173 B2* | 8/2004 | Leser-Reiff et al. ..... 514/231.5 |
| 6,869,953 B2* | 3/2005 | Haag et al. .................. 514/247 |

FOREIGN PATENT DOCUMENTS

| DE | 2 062 265 | 5/1972 |
| EP | 242 851 | 10/1987 |
| EP | 847 992 | 6/1998 |
| FR | 2 167 954 | 8/1973 |
| WO | WO 02/46129 A2 | 6/2002 |
| WO | WO 03/011851 A2 | 2/2003 |
| WO | WO 03/013484 | 2/2003 |

OTHER PUBLICATIONS

Koyama et al., Blood, 96, pp. 1490-1495 (2000).
Rastogi et al., Indian J. chem., 21B, pp. 485-487 (1982).
Moll et al., Z. Chem., 17, pp. 132-134 (1977).
Hassan et al., Indian J. Chem., 39B, pp. 764-768 (2000).
Curtin et al., J. Med. Chem., 41, pp. 74-95 (1998).

* cited by examiner

*Primary Examiner*—Golam M. M. Shameem
(74) *Attorney, Agent, or Firm*—George W. Johnston; Patricia S. Rocha-Tramaloni; Brian C. Remy

(57) ABSTRACT

The present invention relates to compounds of formula I,

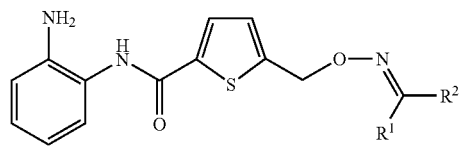

formula I their pharmaceutically acceptable salts as well as their enantiomeric forms, diastereoisomers and racemates; the preparation of the above-mentioned compounds, medicaments containing them and their manufacture, as well as the use of the above-mentioned compounds as inhibitors of histone deacetylase (HDAC) and therefore in the control or prevention of illnesses and disorders as mentioned above, or in the manufacture of corresponding pharmaceutical compositions.

12 Claims, No Drawings

OXIME DERIVATIVES AND THEIR USE AS PHARMACEUTICALLY ACTIVE AGENTS

BACKGROUND OF THE INVENTION

The present invention generally relates to oxime derivatives and pharmaceutically acceptable salts thereof. The invention also relates to processes for the manufacturing of these compounds, to pharmaceutical compositions containing these compounds and to their use in the manufacture of drugs for the treatment of diseases such as cancer.

Cancer is one of the major causes of death, exceeding heart and cerebrovascular diseases, and so many studies have been conducted with enormous expense and time to overcome cancer. However, in spite of a variety of therapies such as surgical operation, radiation therapy and chemotherapy, there is still a great need for improved anticancer therapeutics. Among these therapies, chemotherapy is one of the main areas for cancer treatment. Most drugs show their effect by affecting mainly DNA to express their cytotoxicity and then, in consequence injuring tumor cells. However, lacking selectivity, they do not sufficiently differentiate between tumor cells and normal cells, and therefore, adverse reactions expressed in normal cells have limited their use in therapy. Up to now, no satisfactory drugs have been discovered, and thus an anticancer drug with reduced toxicity, better tolerability and a high therapeutic effect is very much desired.

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and induce apoptosis in several types of cancer cells, including colon cancer cells, T-cell lymphoma cells, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490–1495).

EP-A 0 847 992 describes monoacylated o-phenylendiamine derivatives as cell differentiation inducers. The same type of compounds is also the subject of EP-A 0 242 851. The compounds described in these applications are almost exclusively o-phenylene derivatives monoacylated with derivatives of benzoic acid. WO 03/013484 discloses N-monoacylated carbocyclic but non-aromatic or heteroaromatic o-phenylene diamines as anti-proliferative and differentiation inducing agents. However, there is still a need to provide compounds with improved therapeutical properties such as improved activity, tolerability, selectivity, stability, less toxicity and/or less side effects to name only a few.

Monoacylated o-phenylendiamines are known in the art as precursors for the preparation of the corresponding benzimidazoles, such preparation methods are e.g. described in DE-A 2 062 265; FR 2 167 954; Rastogi, R., and Sharma, S., Indian J. Chem., Sect. B, 21B (5) (1982) 485–487; Moll, R., et al., Z. Chem. 17 (1977) 133–134; and Hassan H., et al., Indian J. Chem. 39B (2000) 764–768.

SUMMARY OF THE INVENTION

It has been found that the compounds of formula I are HDAC inhibitors which have anti-proliferative and differentiation-inducing activity, which results in inhibition of tumor cell proliferation, induction of apoptosis and inhibition of invasion. These compounds are therefore useful for the treatment of diseases such as cancer in humans or animals.

The present invention thus concerns new compounds of the general formula I

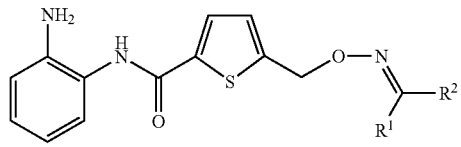

formula I wherein $R^1$ and $R^2$ are as described herewithin, or a pharmaceutically acceptable salt thereof.

The present invention relates to the compounds of formula I, their pharmaceutically acceptable salts as well as their enantiomeric forms, diastereoisomers and racemates; the preparation of the above-mentioned compounds, pharmaceutical compositions containing them and their manufacture, as well as the use of the above-mentioned compounds as inhibitors of histone deacetylase (HDAC) and therefore in the control or prevention of illnesses and disorders as mentioned above, or in the manufacture of corresponding pharmaceutical compositions.

DETAILED DESCRIPTION OF THE INVENTION

The present invention thus concerns new compounds of the general formula I

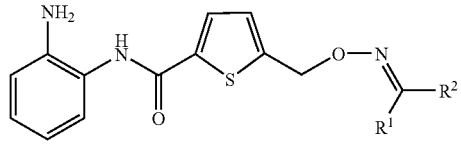

formula I wherein, $R^1$ is hydrogen or $C_1$–$C_4$-alkyl;

$R^2$ is substituted or unsubstituted aryl, substituted or unsubstituted heteroaryl or substituted or unsubstituted heterocyclyl; wherein when $R^2$ is substituted by one or more substituents, the substituents are independently selected from alkyl; halogen; —O-alkyl; —NH(alkyl); and —N(alkyl)$_2$; or R¹ and R², together with the carbon atom to which they are bound, form a cyclic hydrocarbon;

or a pharmaceutically acceptable salt thereof.

The following definitions of the general terms used in the present description apply irrespective of whether the terms in question appear alone or in combination.

The term "halogen" denotes fluorine, chlorine, bromine or iodine.

The term "$C_1$–$C_4$-alkyl" denotes a saturated straight- or branched-chain alkyl group containing from 1 to 4 carbon atoms, for example, methyl, ethyl, propyl, isopropyl, n-butyl, i-butyl, 2-butyl, t-butyl.

The term "alkyl" denotes a saturated straight- or branched hydrocarbon containing from 1 to 12 carbon atoms, for example, methyl, ethyl, propyl, isopropyl, n-butyl, i-butyl, 2-butyl, t-butyl, pentyl, hexyl and the like. The alkyl group may optionally be mono or multiple substituted by halogen, preferably fluor such as e.g. trifluoromethyl or pentafluoroethyl and the like.

The term "aryl" denotes an aromatic 6 to 10 membered mono- or bicyclic hydrocarbon, e.g. a phenyl or naphthyl ring, and the like.

The term "heteroaryl" denotes a 5 or 6 membered monocyclic aromatic hydrocarbon, wherein one or two carbon atoms are replaced by oxygen, nitrogen or sulfur. Examples are imidazolyl, pyrazolyl, thiazolyl, oxazolyl, pyridinyl, pyrimidinyl, and the like.

The term "heterocyclyl" denotes a 6 to 10 membered, mono- or bicyclic non-aromatic or partially aromatic hydrocarbon, wherein one or two carbon atoms are replaced by oxygen or nitrogen. Examples are morpholinyl, piperidinyl, 2,3-dihydro-benzofuranyl, benzo[1,3]dioxolyl, 2,3-dihydro-benzo[1,4]dioxinyl or 2,3-dihydro-1H-indolyl, and the like.

A used herein the term "cyclic hydrocarbon" denotes a 9 or 10 membered bicyclic, non-aromatic or partially aromatic hydrocarbon, formed by R¹ and R² together with the carbon atom to which they are bound. Examples are 1,2,3,4-tetrahydro-naphthylidene, indanylidene, and the like.

The term "effective amount" or "therapeutically effective amount" means an amount of at least one compound of the invention, or a pharmaceutically acceptable salt thereof, that significantly mediates an inappropriate activation of src family tyrosine kinases.

The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and quaternary ammonium hydroxides, such as for example, tetramethylammonium hydroxide. The chemical modification of a pharmaceutical compound (i.e. a drug) into a salt is a technique well known to pharmaceutical chemists to obtain improved physical and chemical stability, hygroscopicity, flowability and solubility of compounds. See, e.g., Ansel, H., et. al., Pharmaceutical Dosage Forms and Drug Delivery Systems, 6th ed., 1995, at pp. 196 and 1456–1457.

An embodiment of the invention are the compounds of formula I, wherein
R¹ is hydrogen;
R² is pyridinyl;
  2,3-dihydro-benzo[1,4]dioxine-6-yl;
  benzo[1,3]dioxole-5-yl; or
  phenyl, which may optionally be once or several times substituted with
halogen;
—O-alkyl;
—NH(alkyl); or
—N(alkyl)₂;

and pharmaceutically acceptable salts thereof.
Such compounds are for example
5-(3,4-Dichloro-benzylideneaminooxymethyl)-thiophene-2-carboxylic acid (2-amino-phenyl)-amide;
5-Benzylideneaminooxymethyl-thiophene-2-carboxylic acid (2-amino-phenyl)-amide;
5-(Benzo[1,3]dioxol-5-ylmethyleneaminooxymethyl)-thiophene-2-carboxylic acid (2-amino-phenyl)-amide;
5-(4-Chloro-benzylideneaminooxymethyl)-thiophene-2-carboxylic acid (2-amino-phenyl)-amide;
5-(3,4-Dimethoxy-benzylideneaminooxymethyl)-thiophene-2-carboxylic acid (2-amino-phenyl)-amide;
5-(4-Fluoro-benzylideneaminooxymethyl)-thiophene-2-carboxylic acid (2-amino-phenyl)-amide;
5-(2-Fluoro-benzylideneaminooxymethyl)-thiophene-2-carboxylic acid (2-amino-phenyl)-amide;
5-(3-Methoxy-benzylideneaminooxymethyl)-thiophene-2-carboxylic acid (2-amino-phenyl)-amide;
5-(2,3-Dihydro-benzo[1,4]dioxin-6-ylmethyleneaminooxymethyl)-thiophene-2-carboxylic acid (2-amino-phenyl)-amide;
5-(4-Trifluoromethoxy-benzylideneaminooxymethyl)-thiophene-2-carboxylic acid (2-amino-phenyl)-amide;
5-(4-Trifluoromethyl-benzylideneaminooxymethyl)-thiophene-2-carboxylic acid (2-amino-phenyl)-amide;
5-(4-Diethylamino-benzylideneaminooxymethyl)-thiophene-2-carboxylic acid (2-amino-phenyl)-amide;
5-(4-Dibutylamino-benzylideneaminooxymethyl)-thiophene-2-carboxylic acid (2-amino-phenyl)-amide; or
5-(Pyridin-3-ylmethyleneaminooxymethyl)-thiophene-2-carboxylic acid (2-amino-phenyl)-amide.

Another embodiment of the invention are the compounds of formula I, wherein
R¹ is $C_1$–$C_4$-alkyl;
R² is phenyl or 2,3-dihydro-benzofuran-4-yl; both of which are optionally once or several times substituted with halogen;
alkyl; or
—O-alkyl;

and pharmaceutically acceptable salts thereof.
Such compounds are for example
5-[1-(4-Propyl-phenyl)-ethylideneaminooxymethyl]-thiophene-2-carboxylic acid (2-amino-phenyl)-amide;
5-[1-(2-Methyl-2,3-dihydro-benzofuran-4-yl)-ethylideneaminooxymethyl]-thiophene-2-carboxylic acid (2-amino-phenyl)-amide;
5-[1-(2,4-Dichloro-phenyl)-ethylideneaminooxymethyl]-thiophene-2-carboxylic acid (2-amino-phenyl)-amide;
5-[1-(3,4-Dichloro-phenyl)-ethylideneaminooxymethyl]-thiophene-2-carboxylic acid (2-amino-phenyl)-amide;
5-[1-(3,4-Dimethoxy-phenyl)-ethylideneaminooxymethyl]-thiophene-2-carboxylic acid (2-amino-phenyl)-amide;
5-(1-Phenyl-ethylideneaminooxymethyl)-thiophene-2-carboxylic acid (2-amino-phenyl)-amide; or 5-[1-(4-Fluoro-phenyl)-ethylideneaminooxymethyl]-thiophene-2-carboxylic acid (2-amino-phenyl)-amide.

Yet another embodiment of the invention are the compounds of formula I, wherein $R^1$ and $R^2$, together with the carbon atom to which they are bound form a cyclic hydrocarbon;

and pharmaceutically acceptable salts thereof.

Such compounds are for example 5-(Indan-2-ylideneaminooxymethyl)-thiophene-2-carboxylic acid (2-amino-phenyl)-amide;

5-(Indan-2-ylideneaminooxymethyl)-thiophene-2-carboxylic acid (2-amino-phenyl)-amide hydrochloride;

5-(Indan-2-ylideneaminooxymethyl)-thiophene-2-carboxylic acid (2-amino-phenyl)-amide methanesulfonate; or 5-(Indan-1-ylideneaminooxymethyl)-thiophene-2-carboxylic acid (2-amino-phenyl)-amide.

An oxime derivative of the formula I, or a pharmaceutically-acceptable salt thereof, may be prepared by any process known to be applicable to the preparation of chemically-related compounds. Such processes, when used to prepare oxime derivative of the formula I, or a pharmaceutically-acceptable salt thereof, are provided as a further feature of the invention and are illustrated by the following representative examples in which, unless otherwise stated, $R^1$ and $R^2$ have the meanings defined above. Starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

A preferred method, and yet another embodiment of the invention is the process for the manufacture of the compounds of formula I, wherein (a) a compound of formula II

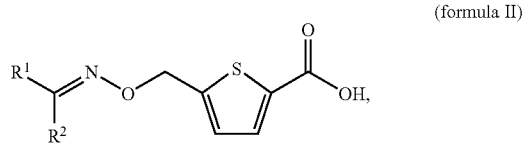

(formula II)

wherein $R^1$ and $R^2$ are as defined above,
is reacted with a compound of the formula III

(formula III)

wherein Y represents hydrogen or a suitable amino protecting group;

(b) the amino protecting group in Y, if present, is cleaved to give a compound of formula I; and (c) said compound of formula I is isolated from the reaction mixture and, if desired, turned into a pharmaceutically acceptable salt.

The "amino protecting groups" as used herein are known from peptide chemistry. Such protecting groups are for example, benzyloxycarbonyl (cleavage by hydrogenation or hydrobromic acid in acetic acid), t-butoxycarbonyl (cleavage by strong acids, such as trifluoroacetic acid (neat or in dichloromethane) or hydrochloric acid (HCL) in dioxane), 9-fluorenmethoxycarbonyl (cleavage by secondary amines, such as, piperidine).

The reaction typically involves a two-step one-pot procedure. In the first step, the carboxylate of the formula II is activated by reaction of the compound in an inert solvent or diluent, for example, in dichloromethane, dioxane, or tetrahydrofuran (THF), in the presence of an activating agent.

A suitable reactive derivative of an acid is, for example, an acyl halide, for example an acyl chloride formed by the reaction of the acid and an inorganic acid chloride, for example thionyl chloride or oxalic acid dichloride; a mixed anhydride, for example an anhydride formed by the reaction of the acid and a chloroformate such as isobutyl chloroformate; an active ester, for example an ester formed by the reaction of the acid and a phenol such as pentafluorophenol; an active ester formed by the reaction of the acid and N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as N-3-dimethylaminopropyl-N-ethylcarbodiimid or dicyclohexylcarbodiimide; or the product of the reaction of the acid with N,N'-carbonyldiimidazole; or the product of the reaction of the acid and uroniumsalts such as O-(1H-benzotriazol-1-yl)-N,N,N',N',-tetramethyl-uronium tetrafluoroborate; or the product of the reaction of the acid and phosphorus based reagents, e.g. bis-(2-oxo-3-oxazolidinyl)-phosphorylchloride. The reaction is carried out between −30° C. and 60° C., conveniently at or below 0° C.

In the second step, compound III is added to the solution containing the activated acid. If Y is a protecting group it finally has to be cleaved (methods see above) to yield a compound of formula I.

These methods are well known to those skilled in the art. In principle, all methods for the synthesis of amides as used in peptide chemistry as described e.g. by Houben-Weyl, In: Methoden der organischen Chemie, Vols. XV/1 and XV/2, are also applicable. Monoacylation of unprotected phenylene diamine is described in EP 0 974 576.

Compounds of formula II can be prepared by cleavage of the $R^3$ group of compounds of formula IV

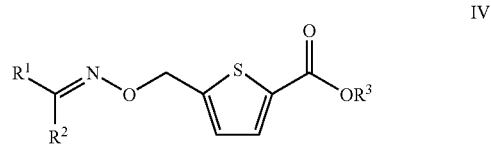

IV wherein $R^3$ is alkyl and said alkyl has the significance given herein before. Examples for $R^3$ are methyl and ethyl. The reaction is carried out in the presence of a base, for example, lithium hydroxide, sodium hydroxide, or potassium hydroxide in an inert solvent or diluent, for example in methanol, ethanol, dioxane, THF, water.

Compounds of the general formula IV can be prepared for example by a substitution reaction of oximes of the general formula V

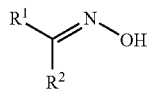
V with a compound of the general formula VI

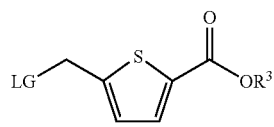
VI wherein LG is a suitable leaving group for this substitution; examples for LG are Br, Cl, I, tosylate, mesylate.

The reaction is carried out in an inert solvent, for example in dichloromethane, acetone, dimethylformamide (DMF), THF, acetonitrile, ethyl acetate, dimethyl sulfoxide (DMSO) and preferably in the presence of a base, e.g. potassium carbonate ($K_2CO_3$), sodium hydroxide (NaOH), sodium hydride (NaH). Addition of potassium iodide or tetrabutylammonium hydrogen sulfate to the reaction mixture may have a favourable effect in certain cases. If necessary the reaction mixture is heated.

A number of compounds of the general formula V are commercially available. In other cases they can be prepared by known methods e.g. condensation reaction of the corresponding aldehydes or ketones VII

with hydroxylamine or hydroxylamine hydrochloride in an inert solvent e.g. ethanol, methanol, water, dioxane and preferably in the presence of a base e.g. pyridine, potassium hydroxide, sodium hydroxide, sodium acetate. If necessary the reaction mixture is heated.

Some compounds of formula VI are described in the literature. For example 5-Bromomethyl-thiophene-2-carboxylic acid methyl ester is described in e.g Curtin, M. L., et al., J. Med. Chem. 41 (1998) 74–95.

The compounds of the general formula I can contain one or several chiral centres and can then be present in a racemic or in an optically active form. The racemates can be separated according to known methods into the enantiomers. Preferably diastereomeric salts which can be separated by crystallization are formed from the racemic mixtures by reaction with an optically active acid such as e.g. D- or L-tartaric acid, mandelic acid, malic acid, lactic acid or camphorsulfonic acid. Furthermore, the racemic compounds can be separated into their enantiomers by chromatography on an analytical, semipreparative or preparative scale using suitable optically active stationary phases with suitable eluents. Suitable optically active stationary phases include, but are not limited to, silica (e.g. ChiraSper,Merck; Chiralpak OT/OP, Baker), cellulose esters or carbamates (e.g. Chiracel OB/OY, Baker) or others (e.g. Crownpak, Daicel or Chiracel OJ-R, Baker).

The compounds of formula I, as well as their pharmaceutically usable addition salts possess valuable pharmacological properties. It has been found that they possess antiproliferative and differentiation-inducing activity, which results in inhibition of tumor cell proliferation, induction of apoptosis and inhibition of invasion. Therefore these compounds are useful for the treatment of diseases such as cancer in humans or animals. Consequently a further embodiment of the present invention is the use of a compound of formula I for the treatment of cancer. Yet another embodiment is the use of a compound of formula I for the manufacture of corresponding medicaments for the inhibition of tumor growth.

The activity of the compounds according to this invention as HDAC inhibitors is demonstrated using a cellular acetylation assay. Therein acetylation of histones is monitored in PC3 cells. High acetylation correlates with inhibition of histone deacetylase by compounds. Cell viability is monitored in parallel to estimate the cytotoxicity of compounds.

PC3 cells, a human prostate carcinoma cell line, are seeded as 1800 cells per well of a 384-well microtiterplate in RPMI 1640 (including 5% FCS, 2 mM glutamine and pen/strep). After 48 h at 37° C. pre-diluted compounds are added to a final concentration of 1 uM. Compounds are pre-diluted in dimethyl sulfoxide (DMSO) resulting in a final concentration of DMSO of 0.5% per well.

After 24 h incubation cell viability is determined by adding cell proliferation reagent WST-1 (Roche Molecular Biochemicals). Another 60 min later the optical density (OD) is measured (450 nm versus 690 nm).

After measurement the cell layer is prepared for the ELISA reaction. Medium is aspirated and cells are fixed in ethanol at −20° C. for 60 min. After washing with PBS/Tween the blocking solution (PBS/5% FCS/Tween) is added and the cell layer is washed again. Antibodies against acetylated histone H3 or H4 (rabbit polyklonal IgG, Upstate Biotechnologie) are added at a dilution of 1:200 for 60 min at 37° C. As a second antibody goat anti rabbit IgG (H+L) humanIgG adsorbed-HRP conjugate (Dako) is used (1:2000 diluted). Cells are washed 3 times and the peroxidase substrate ABTS is allowed to react for 30–60 min at 37° C. The OD is measured at 405 nm.

The percentage of acetylation is calculated after substraction of blank O.D.s:

$$\frac{\frac{\text{mean } O.D. \text{ acetylation}}{\text{mean } O.D. \text{ WSTI}}}{\text{mean } O.D. \text{ DMSO control}} \times 100\%$$

| Ex-No. | Compound Name | cell acetylation (PC3, 1 μM) [% of control] |
|---|---|---|
| | 4-acetylamino-N- (2-amino-phenyl)-benzamide (Reference Compound, from EP0242851, Example 1) | 152 |
| 4–6 | 5-Benzylideneaminooxymethyl-thiophene-2-carboxylic acid (2-amino-phenyl)-amide | 180 |
| 4–7 | 5-(Indan-2-ylideneaminooxymethyl)-thiophene-2-carboxylic acid (2-amino-phenyl)-amide | 182 |

-continued

| Ex-No. | Compound Name | cell acetylation (PC3, 1 μM) [% of control] |
|---|---|---|
| 4–9 | 5-[1-(3,4-Dimethoxy-phenyl)-ethylideneaminooxymethyl]-thiophene-2-carboxylic acid(2-amino-phenyl)-amide | 158 |
| 4–12 | 5-(3,4-Dimethoxy-benzylideneaminooxymethyl)-thiophene-2-carboxylic acid(2-amino-phenyl)-amide | 137 |
| 3 | 5-(2,3-Dihydro-benzo[1,4]dioxin-6-ylmethyleneaminooxymethyl)-thiophene-2-carboxylic acid (2-amino-phenyl)-amide | 116 |
| 4–17 | 5-(4-Trifluoromethoxy-benzylideneaminooxymethyl)-thiophene-2-carboxylic acid(2-amino-phenyl)-amide | 127 |
| 4–21 | 5-(Pyridin-3-ylmethyleneaminooxymethyl)-thiophene-2-carboxylic acid(2-amino-phenyl)-amide | 135 |

The effect of the compounds according to the present invention may further be assessed by the following test:

Male NMRI nu/nu-mice(n=15 per group), aged 8–10 weeks, were subcutaneously injected with $5*10^6$ PC-3 prostate carcinoma cells. On day 10, animals with tumor volumes of about 150 mm$^3$ were randomly assigned to treatment groups. The test compound was administered as a microsuspension in 7.5% gelatine—0.22% NaCl-Suspension with an application volume of 10 ml/kg based on actual body weights. Once daily oral treatment was performed from approximately day 10 to day 27 on a, 5–7 times per week treatment schedule.

The volume of the tumor is determined from the following equation:

Volume of a tumor=½ab$^2$, where "a" and "b" are the long and the short diameters of the tumor, respectively Still another embodiment of the invention is a medicament containing as an active ingredient a compound of formula I as described herein before, if desired together with pharmaceutically acceptable adjuvants. Said medicaments, e.g. in the form of pharmaceutical preparations, can be administered orally, e.g. in the form of tablets, coated tablets, dragees, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Preferred pharmaceutical preparations comprise the following:

| a) Tablet Formulation (Wet Granulation): | | | | |
|---|---|---|---|---|
| Item | Ingredients | | mg/tablet | |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| b) Capsule Formulation: | | | | |
|---|---|---|---|---|
| Item | Ingredients | | mg/capsule | |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

The dosage depends on various factors such as manner of administration, species, age and/or individual state of health.

The following examples and references are provided to aid the understanding of the present invention, the true scope of which is set forth in the appended claims. It is understood that modifications can be made in the procedures set forth without departing from the spirit of the invention.

In the following examples, unless otherwise stated:
i) evaporations were carried out by rotary evaporation in vacuo and work-up procedures were carried out after removal of residual solids such as drying agents by filtration;
(ii) operations were carried out at ambient temperature, that is in the range 18–25° C. and under an atmosphere of an inert gas such as argon or nitrogen;
(iii) column chromatography (by the flash procedure) and high pressure liquid chromatography (HPLC) were performed on Merck Kieselgel silica or Merck Lichroprep RP-18 reversed-phase silica obtained from E. Merck, Darmstadt, Germany;
(iv) yields are given for illustration only and are not necessarily the maximum attainable;
(v) melting points were determined using a Mettler SP62 automatic melting point apparatus, an oil-bath apparatus or a Kofler hot plate apparatus;

(vi) the structures of the products of the formula I were confirmed by nuclear (generally proton) magnetic resonance (NMR) and mass spectral techniques (Micromass Platform II machine using APCI or Micromass Platform ZMD using electrospray);
(vii) intermediates were not generally fully characterized and purity was assessed by thin layer chromatography;
(viii) the following abbreviations have been used:

| | |
|---|---|
| DMF | N,N-dimethylformamide; |
| DMSO | dimethylsulphoxide; |
| THF | tetrahydrofuran; |
| MeOH | methanol; |
| HCl | hydrochloric acid; |
| NaH | sodium hydride |
| $CH_2Cl_2$ | dichloromethane; |
| $H_2SO_4$ | sulphuric acid |
| sat. | saturated |
| sol. | solution |
| h | hour |
| d | days |
| rt | room temperature |
| eq | equivalent |
| mp | melting point [° C.] |
| MW calc'd | molecular weight, calculated [g/mol] |
| MW found | molecular weight, determined by mass spectrometry [g/mol] |

EXAMPLE 1

5-(2,3-Dihydro-benzo[1,4]dioxin-6-ylmethyleneaminooxymethyl)-thiophene-2-carboxylic acid methyl ester To a solution of 500 mg (2.13 mmol) 5-bromomethyl-thiophene-2-carboxylic acid methyl ester and 381 mg (2.13 mmol) 2,3-dihydro-benzo[1,4]dioxine-6-carbaldehyde oxime in 2 ml dichloromethane were added 2.0 ml 2.2M aqueous sodium hydroxide solution and 902 mg (2.55 mmol) tertrabutylammonium hydrogen sulfate while vigorously stirring. After 10 minutes another 2.0 ml 2.2M aqueous sodium hydroxide solution and 902 mg (2.55 mmol) tertrabutylammonium hydrogen sulfate were added. This procedure was repeated one more time. After 20 minutes 8 ml saturated aqueous bicarbonate solution was added. The aqueous phase was extracted three times with ethyl acetate and the combined organic phases were washed with brine and dried over $Na_2SO_4$. The solvent was evaporated and the residue was subjected to silica gel chromatography (hexane/ethyl acetate 4:1, then 3:1) to yield 214 mg (0.64 mmol) 5-(2,3-Dihydro-benzo[1,4]dioxin-6-ylmethyleneaminooxymethrl)thiophene-2-carboxylic acid methyl ester; exact MW [M+H] calc'd: 334.07; MW found [M+H]: 334.2.

EXAMPLE 2

5-(2,3-Dihydro-benzo[1,4]dioxin-6-ylmethyleneaminooxymethyl)-thiophene-2-carboxylic acid To a solution of 200 mg (0.60 mmol) 5-(2,3-dihydro-benzo[1,4]dioxin-6-ylmethyleneaminooxymethyl)-thiophene-2-carboxylic acid methyl ester in 2.4 ml THF were added 1.2 ml 1M aqueous LiOH solution and the reaction mixture was heated to 70° C. for 5 h. Water was added, the mixture was acidified and extracted with ethyl acetate. The combined organic phases were washed with brine, dried over $Na_2SO_4$ and the solvent was evaporated to give 190 mg (0.59 mmol) 5-(2,3-Dihydro-benzo[1,4]dioxin-6-ylmethyleneaminooxymethyl)-thiophene-2-carbox-ylic acid; exact MW [M+H] calc'd: 320.06; MW found [M+H]: 320.2.

EXAMPLE 3

5-(2,3-Dihydro-benzo[1,4]dioxin-6-ylmethyleneaminooxymethyl)-thiophene-2-carboxylic acid (2-amino-phenyl)-amide A solution of 100 mg (0.31 mmol) 5-(2,3-Dihydro-benzo[1,4]dioxin-6-ylmethyleneaminooxymethyl)-thiophene-2-carboxylic acid, 65 mg (0.47 mmol) 1-hydroxybenzotriazol, 92 mg (0.47 mmol) N'-(3-dimethylaminopropyl)-N-ethyl-carbodiimide and 65 μl (0.47 mmol) triethylamine in 3 ml dichloromethane was stirred for 15 minutes. After addition of 68 mg (0.63 mmol) phenylenediamine the reaction mixture was stirred overnight. The solvent was evaporated and the residue was subjected to preparative HPLC to yield 88 mg (0.21 mmol) 5-(2,3-Dihydro-benzo[1,4]dioxin-6-ylm-ethyleneaminooxymethyl)-thiophene-2-carboxylic acid (2-amino-phenyl)-amide (17); exact MW [M+H] calc'd: 410.12; MW found [M+H]: 410.2. $^1$H-NMR (400 MHz, $(CH_3)_2SO$): δ=9.67 (s, 1H), 8.18 (s, 1H), 7.85 (m, 1H), 7.20 (m, 1H), 7.14–7.09 (m, 3H), 6.97 (m, 1H), 6.91 (m, 1H), 6.77 (m, 1H), 6.58 (m, 1H), 5.29 (s, 2H), 4.90 (s, 2H), 4.26 (m, 4H)

EXAMPLE 4

In an analogous manner to that described in the example 3, and using known methods as described in the literature (e.g. in standard works such as Houben-Weyl, Methoden der Organischen Chemie, Georg Thieme Verlag, Stuttgart; Organic Reactions, John Wiley & Sons, Inc., New York) the following compounds are prepared:

| Cpd. No. | Name | exact MW [M + H] calc'd | MW found [M + H] |
|---|---|---|---|
| 4-1 | 5-[1-(4-Propyl-phenyl)-ethylideneaminooxymethyl]-thiophene-2-carboxylic acid (2-amino-phenyl)-amide | 408.17 | 408.2 |
| 4-2 | 5-[1-(2-Methyl-2,3-dihydro-benzofuran-4-yl)-ethylideneaminooxymethyl]-thiophene-2-carboxylic acid (2-amino-phenyl)-amide | 422.15 | 422.2 |
| 4-3 | 5-[1-(2,4-Dichloro-phenyl)-ethylideneaminooxymethyl]-thiophene-2-carboxylic acid (2-amino-phenyl)-amide | 434.05 | 434.1 |

-continued

| Cpd. No. | Name | exact MW [M + H] calc'd | MW found [M + H] |
|---|---|---|---|
| 4-4 | 5-[1-(3,4-Dichloro-phenyl)-ethylideneaminooxymethyl]-thiophene-2-carboxylic acid (2-amino-phenyl)-amide | 434.05 | 434.3 |
| 4-5 | 5-(3,4-Dichloro-benzylideneaminooxymethyl)-thiophene-2-carboxylic acid (2-amino-phenyl)-amide | 420.03 | 420.3 |
| 4-6 | 5-Benzylideneaminooxymethyl-thiophene-2-carboxylic acid (2-amino-phenyl)-amide<br>$^1$H-NMR(400MHz,(CH$_3$)$_2$SO): δ =9.68(s, 1H), 8.32(s, 1H), 7.87–7.86(m, 1H), 7.66–7.63(m, 2H), 7.45–7.43(m, 3H), 7.22 (m, 1H), 7.10(m, 1H), 6.97(m, 1H), 6.77(m, 1H), 6.58(m, 1H), 5.34(s, 2H), 4.89(s, 2H) | 352.11 | 352.3 |
| 4-7 | 5-(Indan-2-ylideneaminooxymethyl)-thiophene-2-carboxylic acid (2-amino-phenyl)-amide<br>$^1$H-NMR(400MHz,(CH$_3$)$_2$SO): δ =9.66(s, 1H), 7.84(m, 1H), 7.31–7.29(m, 2H), 7.24–7.21(m, 2H), 7.12(m, 1H), 7.10 (m, 1H), 6.97(m, 1H), 6.77(m, 1H), 6.58(m, 1H), 5.28(s, 2H), 4.89(s, 2H), 3.77(s, 4H) | 378.13 | 378.3 |
| 4-8 | 5-(Benzo[1,3]dioxol-5-ylmethyleneaminooxymethyl)-thiophene-2-carboxylic acid (2-amino-phenyl)-amide | 396.1 | 396.2 |
| 4-9 | 5-[1-(3,4-Dimethoxy-phenyl)-ethylideneaminooxymethyl]-thiophene-2-carboxylic acid (2-amino-phenyl)-amide<br>$^1$H-NMR(400MHz,(CH$_3$)$_2$SO): δ =9.67(s, 1H), 7.85(m, 1H), 7.33(m, 1H), 7.24–7.20(m, 2H), 7.10(m, 1H), 7.00–6.95 (m, 2H), 6.77(m, 1H), 6.58(m, 1H), 5.34(s, 2H), 4.89(s, 2H), 3.80(s, 3H), 3.78(s, 3H), 2.19(s, 3H) | 426.15 | 426.2 |
| 4-10 | 5-(1-Phenyl-ethylideneaminooxymethyl)-thiophene-2-carboxylic acid (2-amino-phenyl)-amide | 366.13 | 366.3 |
| 4-11 | 5-(4-Chloro-benzylideneaminooxymethyl)-thiophene-2-carboxylic acid (2-amino-phenyl)-amide | 386.07 | 386.2 |
| 4-12 | 5-(3,4-Dimethoxy-benzylideneaminooxymethyl)-thiophene-2-carboxylic acid (2-amino-phenyl)-amide | 412.13 | 412.2 |
| 4-13 | 5-(4-Fluoro-benzylideneaminooxymethyl)-thiophene-2-carboxylic acid (2-amino-phenyl)-amide | 370.1 | 370.2 |
| 4-14 | 5-(2-Fluoro-benzylideneaminooxymethyl)-thiophene-2-carboxylic acid (2-amino-phenyl)-amide | 370.1 | 370.2 |
| 4-15 | 5-[1-(4-Fluoro-phenyl)-ethylideneaminooxymethyl]-thiophene-2-carboxylic acid (2-amino-phenyl)-amide | 384.12 | 384.3 |
| 4-16 | 5-(3-Methoxy-benzylideneaminooxymethyl)-thiophene-2-carboxylic acid (2-amino-phenyl)-amide | 382.12 | 382.2 |
| 4-17 | 5-(4-Trifluoromethoxy-benzylideneaminooxymethyl)-thiophene-2-carboxylic acid (2-amino-phenyl)-amide<br>$^1$H-NMR(400MHz,(CH$_3$)$_2$SO): δ =9.69(s, 1H), 8.38(s, 1H), 7.87(m, 1H), 7.78(m, 2H), 7.45(m, 2H), 7.23(m, 1H), 7.10 (m, 1H), 6.97(m, 1H), 6.77(m, 1H), 6.58(m, 1H), 5.36(s, 2H), 4.90(s, 2H) | 436.09 | 436.1 |
| 4-18 | 5-(4-Trifluoromethyl-benzylideneaminooxymethyl)-thiophene-2-carboxylic acid (2-amino-phenyl)-amide | 420.1 | 420.2 |
| 4-19 | 5-(4-Diethylamino-benzylideneaminooxymethyl)-thiophene-2-carboxylic acid (2-amino-phenyl)-amide | 423.19 | 423.2 |
| 4-20 | 5-(4-Dibutylamino-benzylideneaminooxymethyl)-thiophene-2-carboxylic acid (2-amino-phenyl)-amide | 479.25 | 479.3 |
| 4-21 | 5-(Pyridin-3-ylmethyleneaminooxymethyl)-thiophene-2-carboxylic acid (2-amino-phenyl)-amide<br>$^1$H-NMR(400MHz,(CH$_3$)$_2$SO): δ =9.69(s, 1H), 8.80(m, 1H), 8.62(m, 1H), 8.40(m, 1H), 8.04(m, 1H), 7.87(m, 1H), 7.47(m, 1H), 7.24(m, 1H), 7.10(m, 1H), 6.97(m, 1H), 6.77 (m, 1H), 6.58(m, 1H), 5.37(s, 2H), 4.91(s, 2H) | 353.11 | 353.1 |
| 4-22 | 5-(Pyridin-4-ylmethyleneaminooxymethyl)-thiophene-2-carboxylic acid (2-amino-phenyl)-amide | 353.11 | 353.1 |
| 4-23 | 5-(Pyridin-2-ylmethyleneaminooxymethyl)-thiophene-2-carboxylic acid (2-amino-phenyl)-amide | 353.11 | 353.1 |
| 4-24 | 5-(Indan-2-ylideneaminooxymethyl)-thiophene-2-carboxylic acid (2-amino-phenyl)-amide hydrochloride | 413.93 | 413.9 |
| 4-25 | 5-(Indan-2-ylideneaminooxymethyl)-thiophene-2-carboxylic acid (2-amino-phenyl)-amide methanesulfonate | 473.57 | 473.6 |
| 4-26 | 5-(Indan-1-ylideneaminooxymethyl)-thiophene-2-carboxylic acid (2-amino-phenyl)-amide | 378.13 | 378.1 |

LIST OF REFERENCES

Ansel, H., et. al., Pharmaceutical Dosage Forms and Drug Delivery Systems, 6th ed., 1995, at pp. 196 and 1456–1457
Curtin, M. L., et al., J. Med. Chem. 41 (1998) 74–95
DE-A 2 062 265
EP 0 974 576
EP-A 0 242 851
EP-A 0 847 992
FR 2 167 954
Hassan, H., et al., Indian J. Chem. 39B (2000) 764–768
Houben-Weyl, In: Methoden der organischen Chemie, Vols. XV/1 and XV/2, Georg Thieme Verlag, Stuttgart
Koyama, Y., et al., Blood 96 (2000) 1490–1495
Moll, R., et al., Z. Chem. 17 (1977) 133–134
Organic Reactions, John Wiley & Sons, Inc., New York
Rastogi, R., and Sharma, S., Indian J. Chem., Sect. B, 21B (5) (1982) 485–487
WO 03/013484

What is claimed is:

1. A compound of formula I

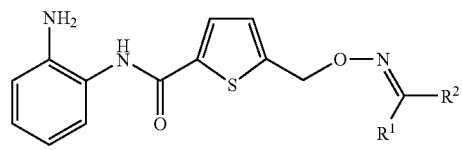

formula I wherein, $R^1$ is hydrogen or $C_1$–$C_4$-alkyl; and
$R^2$ is substituted or unsubstituted aryl, substituted or unsubstituted heteroaryl or substituted or unsubstituted heterocyclyl; wherein when $R^2$ is substituted by one or more substituents, the substituents are independently selected from alkyl; halogen; —O-alkyl; —NH(alkyl); and —N(alkyl)$_2$; or
$R^1$ and $R^2$, together with the carbon atom to which they are bound, form a cyclic hydrocarbon;
or a pharmaceutically acceptable salt thereof.

2. The compound according to claim 1, wherein
$R^1$ is hydrogen; and
$R^2$ is substituted or unsubstituted pyridinyl; substituted or unsubstituted 2,3-dihydro-benzo[1,4]dioxine-6-yl; substituted or unsubstituted benzo[1,3]dioxole-5-yl; or substituted or unsubstituted phenyl, wherein when $R^2$ is substituted by one or more substituents, the substituents are independently selected from halogen; —O-alkyl; —NH(alkyl); or —N(alkyl)$_2$;
or a pharmaceutically acceptable salt thereof.

3. The compound according to claim 1, wherein the compound is
5-(3,4-Dichloro-benzylideneaminooxymethyl)-thiophene-2-carboxylic acid (2-amino-phenyl)-amide;
5-Benzylideneaminooxymethyl-thiophene-2-carboxylic acid (2-amino-phenyl)-amide;
5-(Benzo[1,3]dioxol-5-ylmethyleneaminooxymethyl)-thiophene-2-carboxylic acid (2-amino-phenyl)-amide;
5-(4-Chloro-benzylideneaminooxymethyl)-thiophene-2-carboxylic acid (2-amino-phenyl)-amide;
5-(3,4-Dimethoxy-benzylideneaminooxymethyl)-thiophene-2-carboxylic acid (2-amino-phenyl)-amide;
5-(4-Fluoro-benzylideneaminooxymethyl)-thiophene-2-carboxylic acid (2-amino-phenyl)-amide;
5-(2-Fluoro-benzylideneaminooxymethyl)-thiophene-2-carboxylic acid (2-amino-phenyl)-amide;
5-(3-Methoxy-benzylideneaminooxymethyl)-thiophene-2-carboxylic acid (2-amino-phenyl)-amide;
5-(2,3-Dihydro-benzo[1,4]dioxin-6-ylmethyleneaminooxymethyl)-thiophene-2-carboxylic acid (2-amino-phenyl)-amide; or
5-(4-Trifluoromethoxy-benzylideneaminooxymethyl)-thiophene-2-carboxylic acid (2-amino-phenyl)-amide.

4. The compound according to claim 1, wherein the compound is
5-(4-Trifluoromethyl-benzylideneaminooxymethyl)-thiophene-2-carboxylic acid (2-amino-phenyl)-amide;
5-(4-Diethylamino-benzylideneaminooxymethyl)-thiophene-2-carboxylic acid (2-amino-phenyl)-amide;
5-(4-Dibutylamino-benzylideneaminooxymethyl)-thiophene-2-carboxylic acid (2-amino-phenyl)-amide; or
5-(Pyridin-3-ylmethyleneaminooxymethyl)-thiophene-2-carboxylic acid (2-amino-phenyl)-amide.

5. The compound according to claim 1, wherein
$R^1$ is $C_1$-$C_4$-alkyl; and
$R^2$ is substituted or unsubstituted phenyl or substituted or unsubstituted 2,3-dihydro-benzofuran-4-yl; wherein when $R^2$ is substituted by one or more substituents, the substituents are independently selected from halogen; alkyl; or —O-alkyl;
or a pharmaceutically acceptable salt thereof.

6. The compound according to claim 1, wherein the compound is
5-[1-(4-Propyl-phenyl)-ethylideneaminooxymethyl]-thiophene-2-carboxylic acid (2-amino-phenyl)-amide;
5-[1-(2-Methyl-2,3-dihydro-benzofuran-4-yl)-ethylideneaminooxymethyl]-thiophene-2-carboxylic acid (2-amino-phenyl)-amide;
5-[1-(2,4-Dichloro-phenyl)-ethylideneaminooxymethyl]-thiophene-2-carboxylic acid (2-amino-phenyl)-amide;
5-[1-(3,4-Dichloro-phenyl)-ethylideneaminooxymethyl]-thiophene-2-carboxylic acid (2-amino-phenyl)-amide;
5-[1-(3,4-Dimethoxy-phenyl)-ethylideneaminooxymethyl]-thiophene-2-carboxylic acid (2-amino-phenyl)-amide;
5-(1-Phenyl-ethylideneaminooxymethyl)-thiophene-2-carboxylic acid (2-amino-phenyl)-amide; or
5-[1-(4-Fluoro-phenyl)-ethylideneaminooxymethyl]-thiophene-2-carboxylic acid (2-amino-phenyl)-amide.

7. The compound according to claim 1, wherein
$R^1$ and $R^2$, together with the carbon atom to which they are bound, form a cyclic hydrocarbon;
or a pharmaceutically acceptable salt thereof.

8. The compound according to claim 1, wherein the compound is
5-(Indan-2-ylideneaminooxymethyl)-thiophene-2-carboxylic acid (2-amino-phenyl)-amide;
5-(Indan-2-ylideneaminooxymethyl)-thiophene-2-carboxylic acid (2-amino-phenyl)-amide hydrochloride;
5-(Indan-2-ylideneaminooxymethyl)-thiophene-2-carboxylic acid (2-amino-phenyl)-amide methanesulfonate; or
5-(Indan-1-ylideneaminooxymethyl)-thiophene-2-carboxylic acid (2-amino-phenyl)-amide.

9. A process for making the compound of claim 1, comprising
(a) reacting a compound of formula II

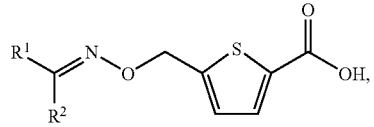
(formula II)

with a compound of the formula III

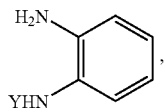
(formula III)

wherein Y represents hydrogen or a suitable amino protecting group.

10. The process according to claim 9, wherein Y is an amino protecting group, further comprising cleaving the amino protecting group to give the compound of formula I.

11. The process according to claim 9, further comprising forming a pharmaceutically acceptable salt of the compound of formula I.

12. A pharmaceutical compositioncomprising:
a compound of forumla I

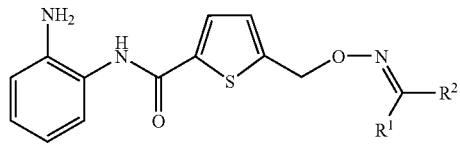
formula I wherein, $R^1$ is hydrogen or $C_1$-$C_4$-alkyl;

$R^2$ is substituted or unsubstituted aryl, substituted or unsubstituted heteroaryl or substituted or unsubstituted heterocyclyl; wherein when $R^2$ is substituted by one or more substituents, the substituents are independently selected from alkyl; halogen; —O-alkyl; —NH(alkyl); and —N(alkyl)$_2$; or $R^1$ and $R^2$, together with the carbon atom to which they are bound, form a cyclic hydrocarbon;

or a pharmaceutically acceptable salt thereof; and
a pharmaceutically acceptable carrier or excipient.

* * * * *